(12) United States Patent
Svensson et al.

(10) Patent No.: US 9,480,815 B2
(45) Date of Patent: Nov. 1, 2016

(54) FLUSHABLE CATHETER AND METHOD FOR PRODUCING SUCH A CATHETER

(75) Inventors: Marie Svensson, Göteborg (SE); Andrea Schmid, Mölnlycke (SE); Stella Salih, Lindome (SE)

(73) Assignee: ASTRA TECH AB, Molndal (SE)

( * ) Notice: Subject to any disclaimer, the term of this patent is extended or adjusted under 35 U.S.C. 154(b) by 208 days.

(21) Appl. No.: 12/888,068

(22) Filed: Sep. 22, 2010

(65) Prior Publication Data
US 2011/0071507 A1 Mar. 24, 2011

Related U.S. Application Data

(60) Provisional application No. 61/244,998, filed on Sep. 23, 2009.

(30) Foreign Application Priority Data

Sep. 23, 2009 (EP) .................................. 09171080

(51) Int. Cl.
| | | |
|---|---|---|
| *A61M 27/00* | (2006.01) | |
| *A61M 25/16* | (2006.01) | |
| *A61M 25/00* | (2006.01) | |
| *A61L 29/04* | (2006.01) | |
| *A61L 29/14* | (2006.01) | |
| *C08B 30/14* | (2006.01) | |
| *C08L 3/02* | (2006.01) | |
| *B29C 65/00* | (2006.01) | |
| *B29L 31/00* | (2006.01) | |

(52) U.S. Cl.
CPC ......... *A61M 25/0017* (2013.01); *A61L 29/043* (2013.01); *A61L 29/046* (2013.01); *A61L 29/148* (2013.01); *A61M 25/001* (2013.01); *A61M 25/0015* (2013.01); *A61M 25/0021* (2013.01); *A61M 27/008* (2013.01); *A61M 2210/1085* (2013.01); *A61M 2210/1089* (2013.01); *B29C 66/73791* (2013.01); *B29C 66/73793* (2013.01); *B29K 2995/006* (2013.01); *B29L 2031/7542* (2013.01); *C08B 30/14* (2013.01); *C08L 3/02* (2013.01); *C08L 2201/06* (2013.01); *C08L 2666/26* (2013.01); *Y10S 220/30* (2013.01)

(58) Field of Classification Search
CPC . A61L 26/0023; A61L 26/009; A61L 27/20; A61L 28/0019; A61L 29/043; A61L 29/045; A61L 29/046; A61L 31/042; A61L 31/045; A61L 31/044; A61L 31/043; A61L 33/08; A61L 33/124; A61L 2300/232; A61L 15/28; A61L 29/148; A61L 29/14; A61L 29/145; D10B 2401/12; A61F 2013/00221; A61F 2013/15252; A61F 2013/51035; A61F 2013/51433; A61F 2013/530313; A61F 2013/530795; C08L 101/16; C08L 2201/06; C08L 3/02; C08L 3/12; C08L 5/02; C08L 5/06; C08B 30/12; C08B 30/14; C08B 30/16; C08B 30/18; C08B 30/20; A61M 2210/1085; A61M 2210/1089; A61M 2210/1092; A61M 2210/1096; A61M 27/008; A61M 25/0017; A61M 25/002; A61M 25/0021; A61M 25/0043
USPC ...... 604/544, 540, 327, 328, 329, 43, 93.01, 604/128, 158, 164.01, 171, 172, 264, 265, 604/275, 523, 288
See application file for complete search history.

(56) References Cited

U.S. PATENT DOCUMENTS

| | | | | |
|---|---|---|---|---|
| 3,954,104 A | * | 5/1976 | Kraskin | A61F 13/26 604/15 |
| 5,350,354 A | * | 9/1994 | Billmers | 604/11 |
| 5,356,149 A | * | 10/1994 | Kane | 473/371 |
| 5,681,873 A | * | 10/1997 | Norton et al. | 523/115 |
| 5,736,209 A | * | 4/1998 | Andersen et al. | 428/36.4 |
| 5,902,262 A | * | 5/1999 | Bastioli et al. | 604/1 |
| 6,063,063 A | * | 5/2000 | Harboe et al. | 604/256 |
| 6,168,857 B1 | * | 1/2001 | Andersen et al. | 428/292.1 |
| 6,319,361 B1 | * | 11/2001 | Smith | D21C 9/005 162/146 |
| 6,808,651 B1 | * | 10/2004 | Katagiri | C08B 37/00 252/194 |
| 2001/0029357 A1 | * | 10/2001 | Bunt et al. | 604/265 |
| 2002/0168518 A1 | * | 11/2002 | Bond | D01F 6/46 428/364 |
| 2002/0168912 A1 | * | 11/2002 | Bond | D01F 8/14 442/415 |
| 2003/0047110 A1 | * | 3/2003 | Poovarodom et al. | 106/124.4 |
| 2003/0135200 A1 | * | 7/2003 | Byrne | 604/544 |

(Continued)

FOREIGN PATENT DOCUMENTS

| | | |
|---|---|---|
| CN | 100402593 C | 7/2008 |
| EP | 0 388 924 A2 | 9/1990 |

(Continued)

*Primary Examiner* — Adam Marcetich
(74) *Attorney, Agent, or Firm* — Birch, Stewart, Kolasch & Birch, LLP

(57) ABSTRACT

A flushable medical device for short term use, such as a urinary catheter, is disclosed, and also a method for producing such a medical device. The medical device comprises at least an elongate shaft made of a degradable material, the degradability being such that the material becomes essentially totally dissolved if maintained in turbulent water at room temperature for at least 6 hours, but retains its structural integrity in water for at least 5 minutes, and preferably at least 10 minutes. Hereby, the medical device can be used for the intended short term use, and then be flushed in an ordinary toilet after use.
The degradable material preferably comprises at least one of monosaccharide, disaccharide, oligosaccharide and polysaccharide. In a preferred embodiment, the degradable material primarily comprises water, at least one of sugar and starch and gelatin.

37 Claims, No Drawings

(56) References Cited

U.S. PATENT DOCUMENTS

| | | | | |
|---|---|---|---|---|
| 2003/0148690 | A1* | 8/2003 | Bond | D01F 8/06 442/338 |
| 2003/0216492 | A1* | 11/2003 | Bowden et al. | 524/47 |
| 2004/0224123 | A1* | 11/2004 | Yano | C08L 67/00 428/98 |
| 2004/0225269 | A1* | 11/2004 | Zhao | A61F 13/26 604/364 |
| 2004/0249021 | A1* | 12/2004 | Hwang et al. | 523/200 |
| 2005/0260316 | A1* | 11/2005 | Wang et al. | 426/516 |
| 2005/0283111 | A1 | 12/2005 | Maurice | |
| 2006/0142736 | A1* | 6/2006 | Hissink et al. | 604/540 |
| 2007/0082982 | A1* | 4/2007 | Noda | A61L 15/28 524/47 |
| 2007/0110799 | A1* | 5/2007 | Leferve et al. | 424/451 |
| 2007/0259413 | A1* | 11/2007 | Tokiwa | C12P 1/06 435/169 |
| 2007/0276317 | A1* | 11/2007 | Henderson et al. | 604/15 |
| 2008/0147034 | A1* | 6/2008 | Wang | A61F 13/15252 604/370 |
| 2008/0213425 | A1* | 9/2008 | Asano et al. | 426/2 |
| 2008/0292666 | A1* | 11/2008 | Hansen | 424/400 |
| 2009/0054548 | A1* | 2/2009 | Wang | C08J 5/18 523/111 |
| 2009/0274920 | A1* | 11/2009 | Li et al. | 428/481 |
| 2010/0015185 | A1* | 1/2010 | Van De Wijdeven | 424/400 |
| 2010/0159170 | A1* | 6/2010 | Wang | B29C 45/0001 428/35.7 |
| 2010/0297458 | A1* | 11/2010 | Khemani et al. | 428/480 |

FOREIGN PATENT DOCUMENTS

| | | |
|---|---|---|
| EP | 0 628 586 A1 | 12/1994 |
| GB | 2 083 762 A | 3/1982 |
| WO | WO 96/41653 A1 | 12/1996 |
| WO | WO 03/059756 A2 | 7/2003 |
| WO | WO 2005/082298 A1 | 9/2005 |
| WO | WO 2006/071813 A2 | 7/2006 |
| WO | WO 2007/035886 A1 | 3/2007 |

* cited by examiner

FLUSHABLE CATHETER AND METHOD FOR PRODUCING SUCH A CATHETER

CROSS REFERENCE TO RELATED APPLICATIONS

This nonprovisional application claims the benefit of U.S. Provisional Application No. 61/244,998 and European Patent Application No. 09171080.6 both filed on Sep. 23, 2009. The entire contents of the above applications are hereby incorporated by reference into the present application.

FIELD OF THE INVENTION

The present invention relates to a flushable medical device for short term use, such as a urinary catheter, as well as a method for producing such a medical device.

BACKGROUND OF THE INVENTION

Many types of medical devices having an elongate shaft for insertion into a body passageway and intended for intermittent or short term use are known, such as urinary catheters for intermittent catheterization, stents, etc. In such medical devices, the shaft, or at least a core substrate of the shaft, is typically made of a durable thermoplastic materials, such as polyethylene, polypropylene or polyvinyl chloride. However, even though said materials are extremely durable, and well suited for the intended use of the medical supplies, their disposal can be problematic, and even hazardous to the environment. For example, thermoplastics such as polyethylene and polypropylene are non-biodegradable and can persist for many years in the environment. Furthermore, such materials are often soiled by biological substances, making recycling of these materials difficult.

Further, medical devices, such as urinary catheters, are often used by users outside hospitals, and even outside the home environment. For example, catheterization may typically take place in public rest rooms. However, in such situations it may often be difficult to find a suitable waste bin for disposal of the catheter after use, and the disposal also involves the risk of unhygienic treatment, spillage etc. Further, disposal of the catheter in a waste bin may also be inconvenient, unpleasant and embarrassing for the user.

There has been attempts to produce similar types of medical devices with degradable material. For example, WO 2006/071813 discloses the use of hydrolytically degradable polymers, for use in medical suppliances, e.g. cannulas, catheters and gloves. However, with this material, the degradation takes very long time, viz. within 6 months after contact with a wetting fluid, which makes the products unsuitable for flushing etc. A similar product is disclosed in EP 0 628 586. Accordingly, these known products does not adequately solve that above-discussed problems.

A problem when flushing a product down in a W.C. is that it must decompose quickly and readily in the sewerage system, otherwise it will give rise to pollution and plumbing problems. Of course, the user must be confident that the device will be flushed and pass through the plumbing system, without causing stoppage and cloggage.

Further, there has been attempts to make bags for human body waste, such as ostomy bags and urine bags, degradable, and even flushable. For example, such bags are disclosed in EP 0 388 924, GB 2 083 762 and EP 1 722 730. However, the therein disclosed materials are not suited for use as medical devices having elongated shafts, such as catheters.

There is therefore a need for flushable disposable medical devices having elongated shafts, such as catheters, that are made from inexpensive starting materials and that can be produced by conventional production processes in order to allow efficient commercialization of such devices.

SUMMARY OF THE INVENTION

It is therefore an object of the present invention to provide a flushable medical device, and a method for producing such a medical device, that alleviates the above-related problems of the prior art.

This object is achieved with a medical device and a method according to the appended claims.

According to a first aspect of the present invention there is provided a flushable, and preferably also biodegradable, medical device for short term use, said medical device comprising an elongate shaft for insertion into a body passageway, wherein at least the elongate shaft is made of a degradable material, the degradability being such that the material becomes essentially totally dissolved if maintained in turbulent water at room temperature for at least 6 hours, but retains its structural integrity in water for at least 5 minutes, and preferably at least 10 minutes.

The term "flushable" is in the context of the present invention used to indicate that degradability is sufficient for the disposable medical device to be flushed into an ordinary toilet without the risk of clogging.

The term "turbulent water" indicates water which is constantly streaming, e.g. by means of agitation, and e.g. with rate of 1000 rpm. Turbulent water is here used as a simulation of flushing a toilet and simulation of flow in vast water pipes.

The term "short term use" indicates a use that is limited in time, and in particular limited to a time period of less than 15 minutes, and preferably less than 10 minutes, and most preferably less than 5 minutes.

The term "biodegradable" is in the context of the present application used to indicate materials that can be broken down by micro organisms into simple stable compounds, such as carbon dioxide and water.

The present invention is based on the surprising finding by the present inventors that it is possible to use a highly hydrolytically degradable material as the base material for a medical device for insertion into a body passageway, such as a urinary catheter. The high degradability of the material makes it possible to flush the medical device into an ordinary WC after use, making the process of handling the device after use highly efficient and convenient for the user. The high degradability ensures that the disposable medical device can be flushed into the toilet without the risk of clogging. At the same time, it has been found that, in spite of the high degradability, the medical device can still retain a sufficient structural integrity for its intended short term use. Hereby, it becomes possible to select a material which has physical and mechanical properties that fit the particular application of interest, such as one or several of the following: being sufficiently rigid, tough, flexible and transparent, and ensuring a high degradability when wetted in e.g. ordinary tap water.

Further, the biodegradable medical device of the present invention may be produced by materials which are environment friendly and non-hazardous. Further, the production can be made without use of any hazardous solvents and the like. In addition, the product can be made essentially free from any solvent residues or the like, since e.g. water can be used instead of other types of solvents.

Still further, the biodegradable medical device of the present invention is highly suitable for very fast production rates, e.g. by means of extrusion.

The new catheter offers very convenient handling of the used catheter, simply by flushing the catheter in the toilet. Further, the catheter can be produced with cost efficient material and cost efficient production. The materials used are also environment friendly, and with a short life reproduction cycle for the raw material, such as sugar, flour, which can easily be produced annually in comparison to synthetic polymers which are produced from crude oil which takes several hundred years to be formed from fossils It has been found by the present inventors that such preferred material constituents may be inexpensive and available in large quantities, making it possible to produce the medical devices at a cost competitive with current non-degradable devices. In a preferred embodiment, the degradable material comprises at least one of monosaccharide, such as glucose and fructose, disaccharide, such as sucrose, and olgio- or polysaccharide, such as starch and cellulose. It is further preferred that the degradable material comprises at least 40% by weight of monosaccharide, disaccharide and/or polysaccharide. Additionally or alternatively, the degradable material may primarily comprise water and at least one of sugar and starch, and wherein the degradable material preferably comprises at least 90% by weight of said constituents.

It is also preferred that the degradable material comprises additives to provide appropriate capacity and properties to the medical device.

For example, additives that may adapt the consistency and elasticity may be used. Such additives are preferably collagen based materials such as gelatin. Other additives that may be used to the same or similar effect are gum Arabic, glycerol, liquorices, salmiak, sugar alcohols such as sorbitol, etc. These additives may be used in combination, or one and one. Materials such as sorbitol and salmiak (ammonium chloride) increase the elasticity thanks to the great capacity to absorb and hold water and moisture. The degradable material preferably comprises this type of additives, such as gelatin, in the range of 0.5-5% by weight, and most preferably 1-3% by weight.

Additives that improve the resistance to dehydration are also preferably incorporated in the degradable material. Such additives may e.g. be various salts, such as sodium chloride. Other salts may also be used in addition to or instead of sodium chloride, such as ammonium chloride.

Additives to improve processability may preferably be used. For example, oils may be added in order to improve processability, e.g. to avoid sticking to the mold or extruder. Such oils that may be used are e.g. olive oil, mineral oil, etc.

Additives to improve the surface finish of the product may also preferably be used. Various additives may be used in this respect, such as bee wax, carnauba wax, etc.

Additives to regulate the acid content and obtain acidic regulation of the product, various acids may preferably be used. Examples of such additives, which may be used alone or in combination, are lactic acid, malic acid, ascorbic acid, tartaric acid, fumaric acid, etc. The acidity is preferably controlled to be below 7 pH, and preferably in the pH range of 4-7, since such an acidicity has proven effective in preventing bacterial growth and inhibit bacterial activity.

Color additives may also preferably be used to obtain any desired color of the end product. Such color additives may e.g. be one or several of curcumin (yellow-orange), carmine (red), chlorophyll (green), caramel color (brown-black), coal (black), carotene (yellow-orange); luetin (yellow); garden beet red (red), anthocyanin (red-blue), calcium carbonate (white), titanium dioxide (white), etc.

Additives with preservative and/or bactericidal properties may also advantageously be used. Such preservatives may improve the capability of storing the products for long time periods, and bactericidal and anti-microbial properties of the medical device are highly advantageous in use, since it reduces the risk of contamination and diseases. Such additives may e.g. be one or several of potassium benzoate, sodium benzoate, potassium sorbate, calcium sorbate, benzoic acid, carbon dioxide, lactic acid, malic acid, ascorbic acid, tartaric acid, fumaric acid, etc.

Other possible constituents are possible as alternative or in addition to the above-mentioned, such as flour, sodium chloride, oil, starch or other polysaccharides and sodium benzoate. Colors, such as color pigment, may also be used to obtain any desired color, even though white or transparent is considered the main alternative. Additives for maintaining high humidity on the surface of the catheter and to maintain low friction during handling in preparation time before catheterization such as polyvinylalcohol (PVA), polyvinylpyrrolidone (PVP) may also be used.

The degradable material preferably also exhibits a low friction surface when wetted. Hereby, low friction properties of the product are automatically achieved, without the need for any additional surface coating or the like, making the medical device very cost effective to produce. Such low friction surfaces are highly advantageous for e.g. urinary catheters, since it enables a very comfortable and easy insertion and retraction of the catheter. However, even though such materials are preferred, it is also possible to use degradable materials which have higher friction when wetted, and provide the low friction properties by additional low friction coatings, or by application of low friction gel or the like before use. Such an additional surface layer of the catheter may be of a low-friction material such as FEP, PTFE or a hydrophilic material such as polyvinylpyrrolidone (PVP).

Preferably, the degradability of the material is such that the material becomes essentially totally dissolved if maintained in water at room temperature for at least 4 hours, and preferably at least 3 hours.

Preferably the elongate shaft is provided with an internal lumen extending through at least the major part of the elongate shaft. This is a highly advantageous structural configuration for e.g. urinary catheters. Preferably, the medical device is a catheter, and most preferably a urinary catheter for intermittent use.

The medical device may comprise additional parts, such as connectors and the like, made of different materials. However, preferably the medical device is made entire of the degradable material.

According to a second aspect of the present invention there is provided a method of manufacturing a medical device, characterized in the steps of:

providing a degradable material, the degradability being such that the material becomes essentially totally dissolved if maintained in water at room temperature for at least 6 hours during agitation; and forming the degradable material into an elongate shaft of said medical device.

Hereby, similar advantages as discussed above in relation to the first aspect of the invention are achieved.

The step of forming the medical device preferably comprises at least one of injection molding, extrusion and melt spinning.

These and other aspects of the invention will be apparent from and elucidated with reference to the embodiments described hereinafter.

DESCRIPTION OF PREFERRED EMBODIMENTS

In the following detailed description, preferred embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of e present invention, it will be apparent to one skilled in the art that the present invention may be practiced without these specific details. In other instances, well known constructions or functions are not described in detail, so as not to obscure the present invention.

The invention will in the following be discussed in the embodiment of a urinary catheter. However, it is to be noted that the same technical teaching may also be used for other types of medical devices insertable into a body passageway, such as other types of catheters, stents, etc.

A urinary catheter conventionally comprises an elongated shaft with a lumen therein. An insertable end of the elongated shaft is provided with draining openings, and the non-insertable end is provided with an outlet, being in fluid connection with the draining openings by means of said lumen. The non-insertable end may additionally comprise a flared rearward end, a separate connector or the like.

The catheter may comprise connection means for connecting the proximal insertion section to a further catheter section or to a urinary collection bag. The connector part may be made from the same material as the elongated shaft, i.e. the proximal insertion section, whereby, at the step of forming the proximal insertion section, the proximal insertion section and the connector part may be formed substantially simultaneously. Alternatively, the connector part may be made from a material different from the material of the proximal insertion section, whereby the connector part and the proximal insertion section are formed in distinct process steps, for example in a multi-component injection molding process.

At least the elongate shaft, and preferably the entire medical device, is made of a degradable material, the degradability being such that the material becomes essentially totally dissolved if maintained in water at room temperature for at least 6 hours during agitation, and preferably already at least 3 hours, but retains its structural integrity in water for at least 10 minutes.

The degradable material is preferably primarily made of sugar and/or starch, and preferably comprises at least one of monosaccharide, disaccharide and polysaccharide. It is further preferred that the degradable material comprises at least 40% by weight of monosaccharide, disaccharide and/or polysaccharide. The content of the catheter material, before solidification, primarily comprise water and at least one of sugar and starch, and wherein the degradable material preferably comprises at least 90% by weight of said constituents. It is also preferred that the degradable material comprises gelatin, and preferably 0.5-5% by weight of gelatin, and most preferably 1-3% by weight of gelatin.

The catheters may be made in various lengths and dimensions. Typically, the elongated shaft for female catheters are in the range of 50-200 mm, such as with a length in the size of 150 mm, and for male catheters may preferably in a length in the range of 180-450 mm, such as in the size of 400 mm.

The degradable catheter may e.g. be produced by means of extrusion, injection molding, or a combination of the two. The injection may take place in a regular machine for injection molding. Depending upon the size and length of the catheter, the injection pressure may be in the range of 500-1500 bar. The mold could be formed to define the body part as an oblong hollow, tubular part with an internal conduit of a size allowing bodily fluid to be drained through the catheter body. As an alternative, the body part could be provided in the form of an oblong solid kernel with one or more vanes extending radially from the kernel and along the entire length thereof. The vanes thus define a number of draining passages for draining urine between the kernel and a bodily draining passage, e.g. the urethra.

If an additional surface coating is to be provided, the mould may be coated with e.g. a hydrophilic material prior to the injection of the degradable material into the mould. As an alternative, series of injections of one or more types of materials into the mould may take place.

For producing a catheter, a fluid material is first injected into a mould and subsequently solidified therein.

EXAMPLES

A degradable catheter according to an exemplary embodiment of the invention was prepared in the following way:

An aqueous solution was prepared with 200 g of sugar dissolved in 233 g water. More specifically, the exemplary embodiment used sugar with about equal parts of a monosaccharide, such as liquid glucose, and disaccharide, such as sucrose. In this example, a combination of equal parts syrup and household sugar were used. The aqueous solution was heated at an elevated temperature, typically about 110° C. After the heating, about 11 g of gelatin dissolved in a small amount of water (5 g) was added to the aqueous solution, and the aqueous solution was heated at the elevated for an additional short period of time, typically 10-15 seconds with stirring.

The aqueous solution was subsequently inserted into a mold, and allowed to cool down, whereby the material is solidified. The catheters were then dried for 2 days at 32° C.

A large number of catheters prepared in the above-discussed way were manufactured, for subsequent testing, as will be discussed in the following. The prepared catheters had a length in the range of 5-30 cm, and a weight in the range of 1.9-7.4 g.

The composition of the material of the final catheter tubes made in this example was as follows:

| Ingredience | Min. wt-% | Max. wt-% | Range wt-% |
| --- | --- | --- | --- |
| Sugar | 28.2 | 31.6 | 28-32 |
| Syrup | 28.3 | 31.4 | 28-32 |
| Gelatine | 3.2 | 3.6 | 3-4 |
| Water | 33.4 | 40.3 | 33-41 |

Notably, a rather wet catheter is preferred over a too dry catheter, since too dry catheters may have a tendency to break. Further, a too dry catheter need to be wetted before use. A catheter having a water content of 33-41% by weight is soft, and does not need any significant additional wetting before use.

Experiment 1

Sterilization

The degradable catheters of the above-discussed type may be sterilized in numerous ways. For example, the degradable catheters may be sterilized by means of electron irradiation, as will be discussed in the following.

Degradable catheters prepared in the way discussed in the foregoing were arranged in closed packages, and were subjected to electron irradiation of 40 kGy radiation dose. The radiation dose is sufficient for ensuring adequate sterilization.

None of the sterilized catheters experienced any noticeable degradation due to the irradiation, and the irradiation induced only minor differences in weight and length. Specifically, the irradiated catheters had an average weight loss of less than 2%, and an average irradiation induced length variation of less than 0.3%. Thus, the radiation induced weight and length variations are negligible.

Accordingly, the degradable catheters are sterilizable at least by means of electron irradiation.

Experiment 2

Dissolving the Catheters

In order to test the ability of the degradable catheters to dissolve in water, 3-4 cm samples of the sterilized catheters were placed in a container together with ordinary tap water. The water had a temperature of 11° C. An ordinary flush in a WC comprises about 6 liters of water, and the amount of water for the test samples were delimited in proportion to the total length of the catheter. Accordingly, the samples were arranged in 350-550 ml of water. The samples were observed when kept in the water during stirring, preferably at 1000 rpm, which simulates a turbulent flow, and it was concluded that for all the samples tested, only small, undissolved parts remained after 1 hour, and after 2-3 hours the tested samples were totally dissolved in the water.

It may consequently be concluded that the degradable catheters are dissolvable in water, and that they are essentially totally dissolved if maintained in water at room temperature for 2-3 hours.

Experiment 3

Mechanical Stability

The integrity and mechanical stability of the degradable catheters after sterilization and initial wetting were also tested. This was made by introducing and retracting the catheters in a urethra model.

The urethra model comprises a transparent PVC tube of internal dimension and length corresponding to a male urethra, arranged on a wooden backdrop, and with openings facing upwards. The catheters tested were inserted to a first opening of the tube, and pushed through the tube and out through the second opening of the tube, simulating the arrival of the catheter insertion end in the bladder.

For this test, the sterilized catheters were first wetted in synthetic urine for 30 seconds. Further, the urethra of the artificial urethra was pre-filled with synthetic urine. After the initial wetting, the catheters were introduced into the "urethra" of the urethra model, all the way up to the "bladder", and within about a minute retracted back again. All the catheters were capable of being both properly introduced into the urethra model, and retracted back again, without any significant damages to the catheters.

Accordingly, it may be concluded that the degradable catheters have the mechanical properties required to function as urinary catheters, and that the degradable catheters maintain their structural integrity for a sufficient time after wetting for their intended use, such as for intermittent catheterization.

Experiment 4

Low Friction Properties

The above-discussed degradable catheters also exhibit a low friction surface when wetted. Conventionally, urinary catheters are often provided with a coating of a hydrophilic coating for providing low friction properties to the catheter after an initial wetting. However, it has surprisingly been found that the above-discussed sugar based material exhibits a very low surface friction, rendering any additional low friction coating superfluous.

Samples of the above-discussed degradable catheters were wetted for 30 seconds, and were subsequently subject to an ocular and manual inspection. For comparison, a commercially available LoFric® catheter, produced by Astra Tech, was also wetted for 30 seconds. In this inspection it was found that the surface of the degradable catheters felt very smooth and slippery. Further, it was found that the degradable catheters, without any coating, exhibited essentially an equally low friction on the surface as the LoFric® catheters.

Further, catheters produced by means of molding were subject to the same testing, with essentially the same positive results.

A specific example for preparation of catheters is discussed in detail below. In addition, other examples are feasible, some of which will now be discussed in some detail. All these examples were found to have similar properties as the ones discussed in the following related to the specific example used for the experimental testing.

Additional Example 1

One exemplary material batch for preparation of catheters was prepared as follows: 25 kg of yellow syrup (47.7 wt-%); 12 kg of wheat flour (22.9 wt-%); 12 liters of water (22.9 wt-%); 1 dl of sodium chloride (NaCl) (0.4 wt-%), 710 g gelatin (1.4 wt-%) and 2.5 liter water to dissolve the gelatin (4.8 wt-%).

In this embodiment, the syrup, flour and water was mixed by stirring without heating until a homogeneous mixture was obtained. The mixture was heated to 90° C. during stirring. NaCl was added and the mixture was heated for 1 hour. Gelative solution (710 g gelatin+2500 g water) was added when the mixture had cooled to 70° C., followed by additional stirring until a homogeneous mixture was obtained. The mixture was poured into buckets which were lubricated with mineral oil. The mixture rested over night and cooled down to room temperature.

This mixture is suitable for extrusion, and was added to a "cold press" screw extruder without temperature zones, and tubes were extruded.

The typical measure of the tubes after drying at 40° C. for 24 hours were inner diameter 3.46+/−0.42 mm, outer diameter 5.66+/−0.27 mm and a wall thickness of 1.26+/−0.21 mm.

Additional Example 2

An alternative exemplary material batch for preparation of catheters, and suitable for extrusion, was prepared as follows: 5 kg yellow syrup (9.4 wt-%); 18 kg wheat flour (33.8 wt-%); 10 kg white household sugar (18.8 wt-%); 20 liters of water (37.6 wt-%); and 216.5 g (1 dl) sodium chloride (NaCl) (0.41 wt-%).

Syrup, four and water was mixed by stirring without heating until a homogeneous mixture was obtained. The mixture was heated to 90° C. during stirring. NaCl was added and the mixture was heated for 1 hour. The mixture was poured into buckets which were lubricated with mineral oil. The mixture rested over night and cooled down to room temperature.

This mixture is suitable for extrusion, and was added to a "cold press" screw extruder without temperature zones, and tubes were extruded.

The typical measure of the tubes after drying at 40° C. for 24 hours were inner diameter 3.64+/−0.22 mm, outer diameter 5.91+/−0.25 mm and a wall thickness of 1.30+/−0.17 mm.

Additional Example 3

One other exemplary material batch for preparation of catheters also suitable for extrusion is similar to the mixture discussed above as Additional example 1, but with slightly different proportions.

This example was prepared as follows: 25 kg of yellow syrup (53.4 wt-%); 12 kg of wheat flour (25.6 wt-%); 8 liters of water (17.1 wt-%); 216.5 g of sodium chloride (NaCl) (0.5 wt-%), 600 g gelatin (1.3 wt-%) and 1 liter water to dissolve the gelatin (2.1 wt-%).

Syrup, flour and water was mixed by stirring without heating until a homogeneous mixture was obtained. The mixture was heated to 90° C. during stirring. NaCl was added and the mixture was heated for 1 hour. Gelatin solution (600 g gelatin+1000 g water) was added when the mixture had cooled to 70° C., followed by additional stirring until a homogeneous mixture was obtained. The mixture was poured into buckets which were lubricated with mineral oil. The mixture rested over night and cooled down to room temperature.

This mixture is also suitable for extrusion, and was added to a "cold press" screw extruder without temperature zones, and tubes were extruded.

This material showed a limited weight loss of 5.4% by weight and a limited loss in length of 1.5% during irradiation. The tubes had an average length of 40 cm and an average weight of 28 g before irradiation.

Additional Example 4

One other exemplary material batch for preparation of catheters also suitable for extrusion is similar to the mixtures discussed above, but where gelatin has been replaced with ammonium chloride (salmiak).

This example was prepared as follows: 60.4 wt-% of yellow syrup; 18.2 wt-% of wheat flour; 17.7 wt-% of water; 0.5 wt-% of sodium chloride (NaCl); and 3.2 wt-% of ammonium chloride.

The catheters with this material composition was prepared in a similar way as discussed in relation to the previously discussed examples, and exhibited similar properties.

As a further example, ammonium chloride may be exchanged by a sugar alcohol, such as sorbitol.

Discussion of Possible Alterations of the Above-Discussed Mixtures

The wheat flour may be completed and or replaced by e.g. corn flour.

Additives that may be added to adapt the consistency and elasticity are e.g. collagen based materials such as gelatin. Other additives that may be used to the same or similar effect are gum Arabic, glycerol, liquorices, salmiak, sugar alcohols such as sorbitol, etc. These additives may be used in combination, or one and one. Materials such as sorbitol and salmiak (ammonium chloride) increase the elasticity thanks to the great capacity to absorb and hold water and moisture.

Additives that improve the resistance to dehydration are e.g. various salts, such as sodium chloride. Other salts may also be used in addition to or instead of sodium chloride, such as ammonium chloride.

Oils may be added in order to improve processability, e.g. to avoid sticking to the mold or extruder. Such oils that may be used are e.g. olive oil, mineral oil, etc.

In order to improve the surface finish of the product, various additives may be used, such as bee wax, carnauba wax, etc.

In order to regulate the acid content and obtain acidic regulation of the product, various acids may be used, alone or in combination, such as one or several of lactic acid, malic acid, ascorbic acid, tartaric acid, fumaric acid, etc. The acidity is preferably controlled to be below 7 pH, and preferably in the pH range of 4-7, since such an acidity has proven effective in preventing bacterial growth and inhibit bacterial activity.

Color additives may be used to obtain any desired color of the end product. Such color additives may e.g. be one or several of curcumin (yellow-orange), carmine (red), chlorophyll (green), caramel color (brown-black), coal (black), carotene (yellow-orange); luetin (yellow); garden beet red (red), anthocyanin (red-blue), calcium carbonate (white), titanium dioxide (white), etc.

Preservatives may also be added, in order to improve the capability of storing the products for long time periods, and for providing bactericidal and anti-microbial properties to the medical device. Such preservatives may e.g. be one or several of potassium benzoate, sodium benzoate, potassium sorbate, calcium sorbate, benzoic acid, carbon dioxide, lactic acid, malic acid, ascorbic acid, tartaric acid, fumaric acid, etc.

Specific embodiments of the invention have now been described. However, several alternatives are possible, as would be apparent for someone skilled in the art. For example, other types of degradable materials having similar properties may also be used. Such and other obvious modifications must be considered to be within the scope of the present invention, as it is defined by the appended claims.

The invention claimed is:

1. A flushable urinary catheter for short term use, said urinary catheter comprising:
   an elongate shaft for insertion into a body passageway, wherein at least the elongate shaft is made of a degradable material, said degradable material comprising at least 40% by weight of monosaccharide and/or disaccharide, the degradability being such that the material becomes essentially totally dissolved if maintained in turbulent water at room temperature for 6 hours, but retains its structural integrity in water for at least 5 minutes.

2. The urinary catheter of claim 1, wherein the degradability of the material is such that the material becomes essentially totally dissolved if maintained in water at room temperature for 4 hours.

3. The urinary catheter of claim 1, wherein the elongate shaft is provided with an internal lumen extending through at least the major part of the elongate shaft.

4. The urinary catheter of claim 1, wherein the entire urinary catheter is made of the degradable material.

5. The urinary catheter of claim 1, wherein the degradable material primarily comprises water and at least one of sugar and starch, and wherein the degradable material comprises at least 90% by weight of said constituents.

6. The urinary catheter of claim 1, wherein the degradable material comprises an additive to control consistency and elasticity.

7. The urinary catheter of claim 6, wherein the additive is a collagen based material.

8. The urinary catheter of claim 7, wherein the collagen based material is a gelatin.

9. The urinary catheter of claim 1, wherein the degradable material exhibits a low friction surface when wetted.

10. The urinary catheter of claim 1, wherein the urinary catheter retains its physical integrity during an ordinary use sequence, including wetting before catheterization and short term catheterization.

11. The urinary catheter of claim 1, wherein the urinary catheter is able to withstand sterilization, including sterilization by means of radiation.

12. The urinary catheter of claim 11, wherein the urinary catheter is able to withstand sterilization by means of radiation.

13. The urinary catheter of claim 1, wherein the urinary catheter has a shelf life after being subject to sterilization of at least 3 years.

14. The urinary catheter of claim 1, wherein the degradability is provided such that the material becomes essentially totally dissolved if maintained in turbulent water at room temperature for 6 hours, but retains its structural integrity in water for at least 10 minutes.

15. The urinary catheter of claim 1, wherein the degradable material comprises a collagen based material to an amount of 0.5-5% by weight.

16. The urinary catheter of claim 1, the degradable material further comprises additives to regulate the acid content to obtain an acidity to be below 7.

17. The urinary catheter of claim 1, the degradable material further comprises additives to regulate the acid content to obtain an acidity to be in the range 4-7.

18. The urinary catheter of claim 1, wherein the degradable material comprises both monosaccharide and disaccharide.

19. The urinary catheter of claim 1, wherein the degradable material comprises both sugar and starch.

20. The urinary catheter of claim 19, wherein the degradable material comprises at least 40% by weight of sugar and starch.

21. The urinary catheter of claim 1, wherein the degradable material comprises disaccharide.

22. The urinary catheter of claim 21, wherein the degradable material comprises at least 40% by weight of disaccharide.

23. The urinary catheter of claim 1, wherein the degradable material further comprises at least one of sorbitol and ammonium chloride.

24. The urinary catheter of claim 1, wherein the degradable material further comprises sodium chloride.

25. The urinary catheter of claim 1, wherein the elongate shaft of the urinary catheter is made by extrusion.

26. A method of manufacturing a urinary catheter for insertion into a body passageway, comprising the steps of:
providing a degradable material, the degradability being such that the material becomes essentially totally dissolved if maintained in water at room temperature for 6 hours; and
forming the degradable material into an elongate shaft of said urinary catheter,
wherein said degradable material comprises at least 40% by weight of monosaccharide and/or saccharide.

27. The method of claim 26, wherein said step of forming comprises at least one of injection molding, extrusion and melt spinning.

28. The method of claim 26, further comprising the step of forming an end of the elongate shaft into a rounded tip portion, said forming including at least one of injection molding, casting, open die forming and melting.

29. The method of claim 28, further comprising forming of openings in the shaft wall, said step of forming comprising at least one of punching and blank cutting.

30. The method of claim 26, further comprising the step of forming an end of the elongate shaft into a flared connector end, said forming including at least one of injection molding, casting, open die forming and melting.

31. The method of claim 26, wherein the degradable material comprises both sugar and starch.

32. The method of claim 31, wherein the degradable material comprises at least 40% by weight of sugar and starch.

33. The method of claim 26, wherein the degradable material comprises disaccharide.

34. The urinary catheter of claim 33, wherein the degradable material comprises at least 40% by weight of disaccharide.

35. The method of claim 26, wherein the degradable material further comprises at least one of sorbitol and ammonium chloride.

36. The method of claim 26, wherein the degradable material further comprises sodium chloride.

37. The method of claim 26, wherein the elongate shaft of the urinary catheter is made by extrusion.

* * * * *